United States Patent [19]

Lovell

[11] 4,353,907

[45] Oct. 12, 1982

[54] AMIDINO HYDRAZONE . $C_{17}H_{29-35}$ COOH INSECT AND FIRE ANT BAIT FORMULATIONS

[75] Inventor: James B. Lovell, Pennington, N.J.

[73] Assignee: American Cyanamid Co., Stamford, Conn.

[21] Appl. No.: 293,581

[22] Filed: Aug. 14, 1981

Related U.S. Application Data

[63] Continuation-in-part of Ser. No. 125,592, Feb. 28, 1980, abandoned.

[51] Int. Cl.³ .................... C07D 239/18; A01N 9/22
[52] U.S. Cl. .................... 424/251; 542/417
[58] Field of Search .................... 542/417; 260/501.2, 260/404.5 H; 424/251

[56] References Cited

U.S. PATENT DOCUMENTS

| | | | |
|---|---|---|---|
| 3,878,201 | 4/1975 | Tomcufcik | 542/417 |
| 4,087,525 | 5/1978 | Lovell | 424/244 |
| 4,152,436 | 5/1979 | Drabb | 424/251 |
| 4,163,102 | 7/1979 | Lovell | 542/417 |
| 4,191,768 | 3/1980 | Drabb | 424/251 |

OTHER PUBLICATIONS

Frear, Chemistry of the Insecticides, pp. 223–225 (1955).

*Primary Examiner*—Robert Gerstl
*Attorney, Agent, or Firm*—H. G. Jackson

[57] ABSTRACT

Amidino hydrazone . $C_{17}H_{29-35}$ COOH useful in insect and fire ant bait formulations and a composition comprising a solution of 1,5-bis-(alpha,alpha,alpha-trifluoro-p-tolyl)-1,4-pentadien-3-one (1,4,5,6-tetrahydro-5,5-dimethyl-2-pyrimidinyl)hydrazone in a mixture of a fatty acid and an edible oil.

16 Claims, No Drawings

AMIDINO HYDRAZONE . $C_{17}H_{29-35}$ COOH INSECT AND FIRE ANT BAIT FORMULATIONS

This application is a continuation-in-part of Ser. No. 125,592, filed Feb. 28, 1980, abandoned.

The invention is compounds of the formula:

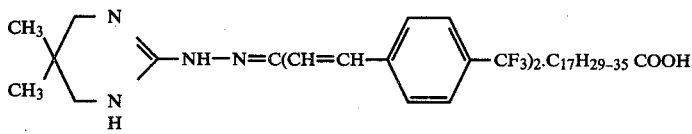

and compositions comprising: a solution of a compound of formula (II):

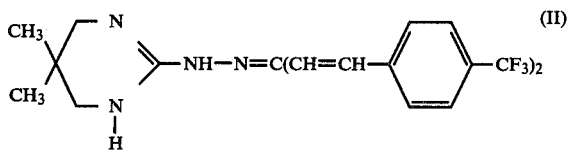

in a mixture of a fatty acid and an edible oil.

The above compound (II): 1,5-bis(alpha,alpha,alpha-trifluoro-p-tolyl)-1,4-pentadien-3-one (1,4,5,6-tetrahydro-5,5-dimethyl-2-pyrimidinyl)hydrazone (hereinafter called amidino hydrazone), is described in U.S. Pat. No. 4,163,102 (1979) as an insecticidal and fire ant control agent. Pentadien-3-one substituted amido hydrazones are described in U.S. Pat. No. 3,878,201 (1975) as antimalarial and antitubercular agents. The above patents are incorporated herein by way of reference.

The compounds (I) and (II) are active as stomach poison and are effective for the control of insects and fire ants such as the southern fire ant, *Solenopsis xyloni*, the black imported fire ant, *Solenopsis richteri* and the red imported fire ant, *Solenopsis invicta*. They are also effective for the control of ants, such as the big-headed ant, *Pheidole megacephala*, and the Argentine ant, *Iridomyrmax humilis*, that are dominant pests in pineapple and sugarcane field, and for the control of many species of ants that are classified under the general category of household ants. Ants are serious economic and public health pests. Serious problems created by fire ants are stinging of humans and livestock, feeding on plants, particularly on seedlings and on germinating seeds, damage to farm machinery that strike ant mounds, loss of crops and refusal of workers to enter infested fields to cultivate and harvest crops. Ants invade houses, crawl over food, carry bits of food to their nests and also cause damage by establishing their nests in the woodwork of houses and other wooden buildings.

Control of these pests can be achieved with treated baits that are distributed in or adjacent to the infested area, such as pasture, park dwellings or other locations in which ant control is desired, and made available to worker ants. The workers carry the treated bait to the colony where it is consumed by the queens and the young ants, leading to their destruction.

The system to deliver the above toxicant to imported fire ants (*Solenopsis invicta* and *Solenopsis richteri*) is critical, since in the anterior portion of the alimentary canal the ants have a filtering mechanism which can filter particles in the range of 2 to 5 microns. Thus, to pass through the filtering system, the toxicant must be either in solution or of a particle size less than 2 to 5 microns to be acceptable to imported fire ants. Moreover, the other components of a suitable delivery system must also be attractive and acceptable to fire ants and preferably act as phagostimulants.

In general, it was found that those edible fats and oils that are attractive to and readily accepted by fire ants, are not very good solvents for the toxicant of formula (I) to allow the preparation of formulations containing the toxicant in concentrations suitable for field applications.

I have now found, that 1,5-bis(alpha,alpha,alpha,-trifluoro-p-tolyl)-1,4-pentadien-3-one-(1,4,5,6-tetrahydro-5,5-dimethyl-2-pyrimidinyl)hydrazone, the compound of formula (II) is readily soluble in fatty acids such as oleic acid, linoleic acid, linolenic acid, stearic acid and mixtures thereof and also reacts with these acids to form salts in concentrations sufficiently high, so that when these are further mixed with and diluted with an edible oil or fat of soybean oil (crude, once refined or twice refined), cotton seed oil, corn oil, coconut oil, olive oil, palm oil, tall oil or mixtures thereof, a formulation results containing the toxicant in concentration suitable for field application.

Conveniently, a composition of the invention may be prepared by dissolving from about 1% to about 10% and preferably 2% to 5% by weight of formulation of 1,5-bis(alpha,alpha,alpha-trifluoro-p-tolyl)-1,4-pentadien-3-one-(1,4,5,6-tetrahydro-5,5-dimethyl-2-pyrimidinyl)hydrazone in a fatty acid of oleic acid, linoleic acid, linolenic acid, stearic acid or mixtures thereof wherein the acid is used in a 1:1 to 2:1 weight ratio and preferably in a 1:1 to 2:1 weight ratio to the toxicant, and at a temperature range of from about 30° C. to about 80° C. and preferably above 50° C. to about 65° C., and then adding to the thus obtained solution an edible oil of soybean oil (crude, once refined or twice refined), cottonseed oil, corn oil, coconut oil, olive oil, peanut oil, palm oil, tall oil or mixtures thereof, in amounts sufficient to total the formulation to 100% by weight.

Thus, for instance, by the above method 5.0 gram of 1,5-bis(alpha,alpha,alpha-trifluoro-p-tolyl)-1,4-pentadien-3-one-(1,4,5,6-tetrahydro-5,5-dimethyl-2-pyrimidinyl)hydrazone is dissolved in 10.0 gram of oleic acid at 55°–65° C. and then 85 gram once refined soybean oil is added and the solution cooled to room temperature to yield a composition containing 5% by weight of toxicant. The formulation is prepared, is ready to be used as is or to put on suitable carriers.

It could be mentioned here, that it is equally feasible to premix the appropriate fatty acid and edible oil, heat the mixture to the desired temperature range as defined above, and then dissolve the appropriate amount of toxicant of formula (II) in the mixture.

In practice, generally about 1.25 g/ha to 75.0 g/ha, and preferably 2.5 g/ha to 37.5 g/ha of the pentadienone hydrazone is effective for fire ant control and/or for crop protection from ants and about 0.0625% to 4% by weight, and preferably 0.125% to 2.0% by weight of the pentadienone hydrazone is effective for the control of house ants.

Baits can be prepared, for example, by placing a composition of the invention in soda straws or on a carrier such as puffed grain, corncob grits, butter and/or starch matrix and distributed in the area of the colony or infestation. Use of these baits has particular advantage, since such method of distribution poses little or no hazard to non-target organisms that may frequent the infested area.

The invention is further illustrated by the examples set forth below. These examples are provided only by way of illustration and are not intended to be limiting.

EXAMPLE 1

Preparation of 1,4-pentadien-3-one, 1,5-bis(alpha,alpha,alpha-trifluoro-p-tolyl)-(1,4,5,6-tetrahydro-5,5-dimethyl-2-pyrimidinyl)hydrazone stearate

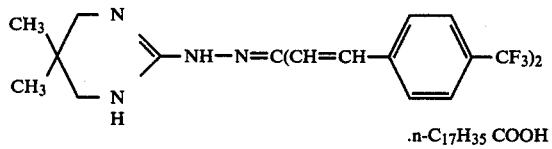

.n-$C_{17}H_{35}$ COOH

A hot solution of 1,5-bis(alpha,alpha,alpha-trifluoro-p-tolyl)-1,4-pentadien-3-one (1,4,5,6-tetrahydro-5,5-dimethyl-2-pyrimidinyl)hydrazone (4.95 g, 0.01 mole,) in 50 ml of ethanol was filtered through a plug of glass wool into a solution of stearic acid (2.85 g, 0.01 mole) in 50 ml of ethanol and the resulting yellow solution stirred several hours at 25° C. The reaction was evaporated in vacuo at 60°–70° C. on a vacuum pump to give 7.22 g (92.6%) of an orange gum, NMR m81-1853 (CDCl$_3$).

Analysis calculated for $C_{43}H_{60}F_6N_4O_2$: C, 66.30; H, 7.76; N, 7.19. Found: C, 65.55; H, 7.69; N, 7.31.

In a similar fashion the following salts were prepared:
Linoleate, .$C_{17}H_{31}$COOH: NMR M81-1854. Anal. calculated for $C_{43}H_{56}F_6N_4O_2$: C, 66.65; H, 7.28; N, 7.23. Found: C, 65.87; H, 7.34; N, 8.05. (94.1% yield).

Linolenate, .$C_{17}H_{29}$COOH: NMR M81-1868. Anal. calculated for $C_{43}H_{54}F_6N_4O_2$: C, 66.82; H, 7.04; N, 7.25. Found: C, 65.98; H, 6.99; N, 8.36. (91.7% yield).

Oleate, .$C_{17}H_{33}$COOH: NMR M81-1928. Anal. calculated for $C_{43}H_{58}F_6N_4O_2$: C, 66.47; H, 7.52; N, 7.21. Found: C, 66.24; H, 7.44; N, 7.55. (98.6% yield).

Determination of Solubility in Soybean Oil

Each salt of example 1 was equilibrated with approximately ⅝ its weight of soybean oil at 100° C. for 4 hours with ultrasonic agitation. The resulting mixtures were centrifuged while hot and allowed to cool to room temperature (25° C.). Excess salts was observed in all cases. Duplicate samples of the oil phases were analyzed by solution in methylene chloride and quantitation by HPLC.

| | SOLUBILITY Amidino Hydrazone Salt Of | | | |
|---|---|---|---|---|
| | Stearic Acid | Linoleic Acid | Linolenic Acid | Oleic Acid |
| Molecular Weight Amidino Hydrazone Content | 284.5 | 280.4 | 278.4 | 282.5 |
| Theory | 63.48% | 63.81% | 63.98% | 63.64% |
| Found | 56.6% | 55.6% | 66.2% | 64.8% |
| | 62.3% | 60.2% | 62.9% | 64.7% |
| | 59.5% Average | 57.9% Average | 64.5% Average | 64.8% Average |
| % of Theory | 93.7% | 90.7% | 100.8% | 101.7% |
| Solubility in Soybean Oil | | | | |
| weight Salt | 0.7572 g | 1.2893 g | 0.7918 g | 1.1515 g |
| Weight Oil | 0.2448 g | 0.4727 g | 0.2403 g | 0.3462 g |
| % Amidino Hydrazone in Oil Layer (w/w) | 29.8% | 30.3% | 35.9% | 27.8% |
| | 30.4% | 30.4% | 34.8% | 28.1% |
| | 30.1% Average | 30.3% Average | 35.4% Average | 28.0% Average |
| % Salt in Oil Layer* | 47% | 47% | 55% | 44% |

*% Salt = % Amidino Hydrazone $\left( \dfrac{\text{m.w salt}}{\text{m.w amidino hydrazone}} \right)$ Insecticide Testing for Compounds of Example 1
Insect: Tobacco budworm (*Heliothis virescens*), egg
Test: Screening, TBW egg test.
Formulation: 50:50 acetone:water.
Concentrations: Screening: 300, 100, 10, 1 ppm.
Plant Preparation: Cotton plants are selected to give plants with the first true leaf expanded to about 6–7 cm in length.
Insect Preparation: Eggs are collected on cheesecloth used as the lid for the moth oviposition chamber in the rearing colony. This cloth is cut into 10–20 mm squares containing about 50–100 budworm eggs laid within the past day. Thus, eggs are 6–30 hours old when used in the test.
Test Procedures: The cotton plant is dipped in the test formulation and agitated for 3 seconds. A square of cheesecloth with eggs is also dipped in the test formulation, placed on the treated leaf and the combination placed in the hood to air dry. When dry, the leaf and egg cloth are removed from the plant, and placed in an "8-ounce Dixie cup (240 ml. 6 cm high, top diameter 9.5 cm. bottom diameter 8 cm)," to which a 5 cm length of damp cotton dental wick had been previously added. A clear plastic lid is placed on the cup.
Holding Conditions: The cups are held at 27° C. until the eggs hatch, which occurs in about 2 days.
Observations: Kill of eggs. This may require the use of a low-power microscope to determine if the lack of visible mobile caterpillars is due to lack of egg hatch or due to the newly hatched caterpillars dying on the leaf under and near the cheesecloth. The standard rating system of 0-9 is used to record the results.

| Ratings | |
|---|---|
| 0 - 0 control | 5 - 60% control |
| 1 - 20% control | 6 - 70% control |
| 2 - 30% control | 7 - 80% control |
| 3 - 40% control | 8 - 90% control |
| 4 - 50% control | 9 - 100% control |

Insect: Tobacco budworm (*Heliothis vireacens*), 1st instar.
Test: Screening, TBW 1st instar test.
Formulation: 50:50 acetone:water
Concentrations: Screening: 300, 100, 10, 1 ppm
Plant Preparation: Cotton plants are selected to give plants with the first true leaf expanded to about 6-7 cm in length.
Insect Preparation: Cheesecloth on which moths have oviposited is daily cut into 10-20 mm squares containing 50-100 eggs each. These squares are held at 21° C. for 2 days and 24° C. for another day in order to coordinate hatch with testing times. Thus, the larvae are 0-2 hours old at time of use.
Test Procedure: The cotton plant is dipped in the test formulation, agitated for 3 seconds, and placed in the hood to air dry. When dry, the leaf is removed from the plant and placed in an "8-ounce Dixie cup (240 ml, 6 cm high, top diameter 9.5 cm, bottom diameter (8 cm)" to which a 5 cm length of damp cotton dental wick had been previously added. A square of cheesecloth with newly hatched budworm larvae on it is placed on the treated leaf and a clear plastic lid is put on the cup.
Holding Conditions: The cups are held at 27° C. for 2 days.
Observations: Kill of larvae. This may require the use of a low-power microscope to determine if the worms are dead or just not feeding. Observation of amount of feeding is also recorded. Where there is only trace to light feeding, the cup is held an extra day and results recorded at that time. The standard rating system of 0-9 is used.
Insect: Bean aphid (*Aphis fabae*), mixed stages.
Test: Screening: bean aphid test
Formulation: 50:50 acetone:water.
Concentrations: 100 ppm.
Plant Preparation: 5 cm pots each containing a nasturtium plant about 5 cm tall are infested with 100 to 400 aphids 2-4 days before the test.
Insect Preparation: See above.
Test Procedure: The pot of aphids is sprayed for 2 revolutions of a 4 rpm turntable in the hood, using a #154 DeVilbiss atomizer at 1500 kg/m$^2$ pressure. The spray tip is held about 15 cm from the plant and the spray directed so as to give complete coverage of the aphid and the plants. The sprayed plants are laid on their sides on white enamel trays measuring 24×34 cm.
Holding Conditions: Trays of sprayed pots are held at 27° C. for 1 day.
Observations: Mortality estimates are made and data recorded with the standard 0-5 rating system.
NOTE: For LD$_{50}$ determinations, a clean tray 24×34 cm is ruled off into a grid with 3 cm spacing and the live aphids gently brushed off the plant onto the gridded tray. This makes it easier to make an exact count of the number of aphids on the plant. Dead aphids, which fall off the plant onto the tray, are counted where they fall, since they stick to the tray and cannot be brushed onto a gridded tray for counting.
Mite: Phosphate resistant 2-spotted spider mite (*Tetranychus urticae*), adults, eggs, nymphs.
Test: Screening: Mite test.
Formulation: 50:50 acetone:water
Concentrations: 300, 100, 10, 1 ppm
Plant Preparation: Sieva lima bean plants with primary leaves 7-8 cm long are selected and cut back to one plant per pot. A small piece is cut off of a leaf taken from the main mite colony and placed on each leaf of the test plants. This is done about 1-3 hours before use to allow the mites to move over to the test plant and lay eggs before treatment. The size of the piece cut is varied to try to obtain about 100 mites per leaf.
Mite Preparation: See above.
Test Procedure: The piece of leaf used to transfer mites is removed and discarded. The mite-infested plant is dipped in the test formulation for 3 seconds with agitation, and the plant set in the hood to dry.
Holding Conditions: The plants are held for 2 days at 27° C. for the first observation, and the second leaf is kept on the plant for another 5 days for the final observation.
Observations: After 2 days one leaf is removed and examined under a 10×microscope to determine the mortality of the adult mites. The second leaf is examined similarly 7 days after treatment to observe the kill of eggs and of newly hatched nymphs giving a measure of ovicidal and residual action, respectively. Any evidence of phytotoxicity from the test treatment is noted. The standard rating system of 0-9 is used to record the mite data.
Insect: Southern armyworm (*Spodoptera eridania*). 3rd instar.
Test: Screening: Southern armyworm larva.
Formulation: 2:1 acetone:water.
Concentrations: 1000, 100, 10, 1 ppm.
Plant Preparation: Sieva lima bean plants are selected with primary leaves 7-8 cm long and cut back to one plant per pot.
Insect Preparation: A 100×10 mm petri dish is prepared by putting a damp filter paper in the bottom and ten 3rd instar larvae are added. These are about 10 mm long.
Test Procedure: The bean plant is dipped for 3 seconds with agitation in the test formulation and placed in the hood to dry. One leaf is removed from the plant and placed in the petri dish with the caterpillars.
Holding Conditions: The dish is held at 27° C. The plant with the remaining leaf is held in the greenhouse under high intensity lights.
Observations: Mortality counts are made after 2 days and recorded using the standard 0-9 rating system.

TABLE I

Insecticide and Acaracide Control Ratings for Compounds of Example 1.

| Compound | Budworm Eggs | Aphids | 3rd Instar Armyworms | P-res. Mites | 1st Instar Tobacco Budworms |
|---|---|---|---|---|---|
| Amidino Hydrazone Oleate | 300 ppm 0 | 100 ppm 0 | 1000 ppm 9 | 300 ppm 0 | 300 ppm 7 |
| | | | 100 ppm 9 | | 100 ppm 0 |
| | | | 10 ppm 6 | | 10 ppm 0 |
| Amidino Hydrazone Linoleate | 300 ppm 0 | 100 ppm 0 | 1000 ppm 9 | 300 ppm 0 | 300 ppm 9 |
| | | | 100 ppm 9 | | 100 ppm 7 |
| | | | 10 ppm 9 | | 10 ppm 0 |
| Amidino Hydrazine Linolenate | 300 ppm 0 | 100 ppm 5 | 1000 ppm 9 | 300 ppm 0 | 300 ppm 9 |
| | | | 100 ppm 9 | | 100 ppm 9 |
| | | | 10 ppm 9 | | 10 ppm 0 |
| Amidino Hydrazone Stearate | 300 ppm 0 | 100 ppm 8 | 1000 ppm 9 | 300 ppm 0 | 300 ppm 9 |
| | | | 100 ppm 9 | | 100 ppm 9 |
| | | | 10 ppm 9 | | 10 ppm 0 |

EXAMPLE 2

Preparation of a formulation comprising the toxicant, linoleic acid and soybean oil A mixture of 1,5-bis(alpha,alpha,alpha-trifluoro-p-tolyl)-1,4-pentadien-3-one-(1,4,5,6-tetrahydro-5,5-dimethyl-2-pyrimidinyl)hydrazone (10.53 g; 95% pure=10.0 g real) and linoleic acid (10.0 g; 65% pure=6.5 g real) is heated at 60° C. until a clear solution is obtained, and then soybean oil (79.47 g; once refined) is added, the mixture stirred and allowed to cool to room temperature. On standing, no precipitate forms and the solution remains clear. An average of four analyses indicates the presence of 9.63% by weight of toxicant in the formulation.

EXAMPLE 3

Preparation of a formulation comprising the toxicant, oleic acid and soybean oil A mixture of 1,5-bis(alpha,alpha,alpha-trifluoro-p-tolyl)-1,4-pentadien-3-one-(1,4,5,6-tetrahydro-5,5-dimethyl-2-pyrimidinyl)hydrazone (10.53 g; 95% pure=10.0 g real) and oleic acid (15.0 g) is heated at 80° C. until a clear solution is obtained. Soybean oil (74.47 g; once refined) is taken added, the mixture stirred and allowed to cool to room temperature. On standing no precipitate forms and the solution remains clear.

EXAMPLE 4

Preparation of various solutions containing the toxicant for evaluation of acceptance by fire ants A. 1,5-Bis(alpha,alpha,alpha-trifluoro-p-tolyl)-1,4-pentadien-3-one-(1,4,5,6-tetrahydro-5,5-dimethyl-2-pyrimidinyl)hydrazone (10.53 g; 95% pure=10.0 g real) and oleic acid (10.0 g) are mixed, then soybean oil (79.47 g; once refined) added and the whole heated to 55° C. until a solution forms. The solution is then cooled to room temperature.

B. The above preparation is repeated excepting that linoleic acid is substituted for oleic acid.

C. A sample of A is diluted with a mixture of oleic acid and soybean oil (used in the same proportions as above) to afford a 5% by weight of solution of the above toxicant.

D. A sample of B is diluted with a mixture of linoleic acid and soybean oil (used in the same proportions as above) to afford a 5% by weight of solution of the above toxicant.

The above prepared samples are then evaluated for acceptance and the data obtained in summarized in Table II below.

Procedure

Each formulation is tested against 4 colonies of field-collected fire ants placed in N20e (5 gal) buckets. A 2.5 cm (1") square of blotting paper on a 5.0 cm (2") square of aluminum foil is impregnated with the formulation and a like piece is impregnated with the same quantity of soybean oil. The squares are placed on opposite sides in the bucket and allowed one minute for orientation of the ants. A 5-minute test is then run and the number of ants on both the formulation square and the soybean oil (standard) square are counted (estimated for large numbers). An acceptance ratio is determined by dividing the total number feeding on the soybean standard.

TABLE II

| Sample | Total No. of Ants Attracted to | | Acceptance Ratio/Average |
|---|---|---|---|
| | Bait formulation | Soybean oil Std. | |
| A | 206 | 53 | 3.90 |
| | 210 | 165 | 1.27 |
| | | | 2.59 |
| B | 37 | 81 | 0.46 |
| | 142 | 152 | 0.93 |
| | | | 0.69 |
| C | 50 | 30 | 1.67 |
| | 325 | 306 | 1.06 |
| | | | 1.37 |
| D | 131 | 82 | 1.60 |
| | 395 | 303 | 1.30 |
| | | | 1.45 |

EXAMPLE 5

Evaluation of the effect of changing the toxicant: Fatty acid ratio of the formulation I. A mixture of 1,5-bis(alpha,alpha,alpha-trifluoro-p-tolyl)-1,4-pentadien-3-one-(1,4,5,6-tetrahydro-5,5-dimethyl-2-pyrimidinyl)hydrazone (10.52 g; 95% pure=10.0 g real), linoleic acid (5.0 g; toxicant:acid ratio=2.1) and soybean oil (84.48 g; once refined) is heated to 55°-60° C. until a clear solution occurs. On cooling, the toxicant crystallizes out of solution.

II. The above preparation is repeated, except that only 1.0 g. linoleic acid (toxicant:acid ratio=10:1) is used. On cooling, the toxicant crystallizes out of solution.

EXAMPLE 6

Preparation of a solution of the toxicant in tall oil

A 1% by weight solution is prepared by dissolving 1,5-bis(alpha,alpha,alpha-trifluoro-p-tolyl)-1,4-pentadien-3-one in tall oil at 65° C. The solution is then cooled down to room temperature. No precipitation of toxicant occurs.

The above prepared sample is evaluated for acceptance by the procedure of Example 4. The data obtained are given in Table III below.

TABLE III

| Total No. of Ants Attracted to | | |
|---|---|---|
| Bait formulation | Soybean oil Std. | Acceptance Ratio/Average |
| 32 | 256 | 0.13 |
| | | 0.08 |
| 8 | 316 | 0.03 |

EXAMPLE 7

Preparation of formulations comprising toxicant, oleic acid and soybean oil

Oleic acid (2.2 g) is heated to 80° C. and 1,5-bis(alpha,alpha,alpha-trifluoro-p-tolyl)-1,4-pentadiene-3-one (1,4,5,6-tetrahydro-5,5-dimethyl-2-pyrimidinyl)hydrazone (1.1 g) is added in small portions with stirring. The resulting solution is then mixed with soybean oil (16.7 g; once distilled) to afford a solution containing the above toxicant in a 5% by weight concentration.

Alternatively, the oleic acid (2.2 g) and soybean oil (16.7 g, once distilled) may be premixed, heated to 80° C. and then 1,5-bis(alpha,alpha,alpha-trifluoro-p-tolyl)-1,4-pentadien-3-one-(1,4,5,6-tetrahydro-5,5-dimethyl-2-pyrimidinyl)hydrazone (1.1 g) added in small portions with stirring to afford a solution containing the toxicant in a 5% by weight concentration.

EXAMPLE 8

Preparation of a bait solution containing 2.5% by weight of toxicant

A mixture of 5% by weight of the formulation of oleic acid (or linoleic acid) and 92.5% by weight of soybean oil (once distilled) are mixed, stirred and heated to 50° C. Next, 2.5% by weight of formulation of 1,5-bis(alpha,alpha,alpha-trifluoro-p-tolyl)-1,4-pentadien-3-one-(1,4,5,6-tetrahydro-5,5-dimethyl-2-pyrimidinyl)hydrazone is added in small portions until a clear solution is obtained.

I claim:

1. Compounds of the formula:

[structure] · $C_{17}H_{29-35}$ COOH

2. A linolenate compound according to claim 1 of the formula:

[structure] · $C_{17}H_{29}$ COOH

3. An oleate compound according to claim 1 of the formula:

[structure] · $C_{17}H_{33}$ COOH

4. A linoleate compound according to claim 1 of the formula:

[structure] · $C_{17}H_{31}$ COOH

5. A stearate compound according to claim 1 of the formula:

[structure] · n-$C_{17}H_{35}$ COOH

6. A liquid composition comprising: a solution of an insecticidal compound of the formula:

[structure]

in a fatty acid of oleic acid, linoleic acid, linolenic acid, stearic acid or mixtures thereof, and an edible oil of crude soybean oil, once refined soybean oil, twice refiner soybean oil, cotton seed oil, corn oil, coconut oil, olive oil, palm oil, tall oil, peanut oil, or mixtures thereof.

7. A composition according to claim 6, comprising 1% to 10% by weight of the composition of the insecticidal compound of the formula:

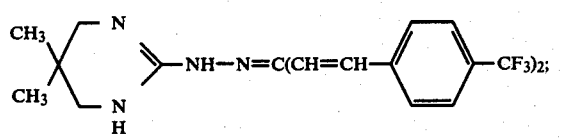

1% to 20% by weight of the composition of a fatty acid of oleic acid, linoleic acid, linolenic acid, stearic acid or mixtures thereof; and 70% to 98% by weight of an edible oil of crude, once, or twice-refined soybean oil, cotton seed oil, corn oil, coconut oil, peanut oil, olive oil, palm oil, tall oil or mixtures thereof.

8. A composition according to claim 7, comprising 2% to 5% by weight of composition of the above insecticidal compound; 4% to 10% by weight of said fatty acid; and 85% to 94% by weight of edible oil.

9. A composition according to claim 7, wherein the fatty acid is oleic acid or linoleic acid; and the edible oil is once refined soybean oil.

10. A composition according to claim 7, comprising 5% by weight of 1,5-bis(α,α,α-trifluoro-p-tolyl)-1,4-pentadien-3-one-(1,4,5,6-tetrahydro-5,5-dimethyl)-hydrazone, 10% by weight of linoleic acid and 85% by weight of once refined soybean oil.

11. A composition according to claim 7 wherein said fatty acid is oleic acid.

12. A composition according to claim 7, comprising 10% by weight of 1,5-bis(α,α,α-trifluoro-p-tolyl)-1,4-pentadien-3-one-(1,4,5,6-tetrahydro-5,5-dimethyl)hydrazone, 10% by weight of oleic acid, and 80% by weight of once refined soybean oil.

13. A composition according to claim 7, wherein said fatty acid is linoleic acid.

14. A method for the preparation of a liquid insecticidal composition comprising: dissolving 1% to 10% by weight of a compound of formula:

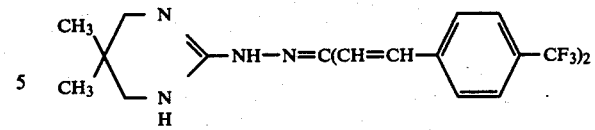

in 1% to 20% by weight of a fatty acid of oleic acid, linoleic acid, linolenic acid, stearic acid or mixtures thereof at a temperature range of from 30° C. to 80° C.; and adding to the solution 70% to 98% by weight of composition an edible oil of crude, once, or twice-refined soybean oil, cottonseed oil, corn oil, coconut oil, olive oil, peanut oil, palm oil, tall oil or mixtures thereof.

15. A method for the preparation of a liquid insecticidal composition comprising: adding 1% to 20% by weight of a fatty acid of oleic acid, linoleic acid, linolenic acid, stearic acid or mixtures thereof to 80% to 99% by weight of an edible oil of crude, once, or twice-refined soybean oil, cottonseed oil, corn oil, coconut oil, olive oil, peanut oil, palm oil, tall oil or mixtures thereof heating the mixture to a temperature range of from 30° C. to 80° C. and dissolving 1% to 10% by weight of a compound of formula:

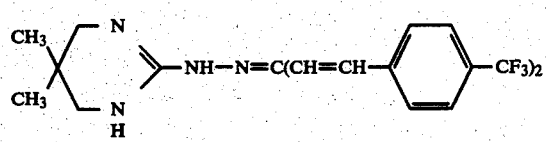

into the mixture.

16. A method for controlling insects and acarina comprising contacting the insects and acarina, their habitat, breeding grounds or feed, with an insecticidally or acaricidally effective amount of a compound of the formula:

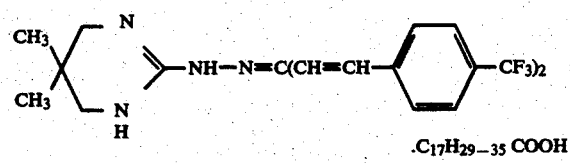

.$C_{17}H_{29-35}COOH$

* * * * *